United States Patent [19]

Davidas

[11] 4,326,305

[45] Apr. 27, 1982

[54] METHOD FOR MAKING ARTIFACTS USABLE IN VIVO AND A ARTIFACTS MADE BY SAID METHOD

[76] Inventor: Jean P. Davidas, 110, rue Lamarck, 75018 Paris, France

[21] Appl. No.: 210,380

[22] Filed: Nov. 26, 1980

[30] Foreign Application Priority Data

Nov. 26, 1979 [FR] France ................................. 79 29038

[51] Int. Cl.³ ........................... A61F 1/24; A61F 1/00
[52] U.S. Cl. ........................................... 3/1.9; 427/2; 433/201; 204/192 C
[58] Field of Search ..................... 3/1.9, 1.91; 427/2; 433/201; 204/192 C

[56] References Cited

U.S. PATENT DOCUMENTS 4,234,972 11/1980 Hench ..................................... 3/1.9

FOREIGN PATENT DOCUMENTS 2717615 10/1978 Fed. Rep. of Germany ........... 3/1.9

*Primary Examiner*—Sam Silverberg
*Attorney, Agent, or Firm*—Darby & Darby

[57] ABSTRACT

An artifact usable in-vivo in general or buccal surgery of the type in which a metallic armature is covered with a coating layer of a biocompatible compound.

The compound is insulating, refractory, amorphous and non porous, and the thickness of the coating layer is between 100 A° and 0.5 micron, whereby the coating layer is adapted for supporting without cracks the deformations of the artifact during the clinical phase.

5 Claims, No Drawings

METHOD FOR MAKING ARTIFACTS USABLE IN VIVO AND A ARTIFACTS MADE BY SAID METHOD

This invention relates to artifacts used in vivo in general or buccal surgery, and to a method for making such artifacts.

The term artifacts is used here as meaning substantially metallic bodies or elements, adapted for being used in surgery for making an intra-osseous or juxta-osseous prosthesis or for the fixation of a buccal prosthesis for example. The invention relates therefore to general surgery (osteo-synthesis) and to buccal surgery (implantology).

The use of metallic artifacts, particularly in implantology, is rather widespread, due to the efficiency and the quality of the fixations they provide for the prosthesis in particular. One of the advantages of such metallic artifacts is that they cause only a negligible mutilation when compared to the large contact surface with the support tissues, which their design allows.

The use of metallic artifacts, in pure or alloyed metal, is nevertheless criticized due to the permanent and intimate relation which is established between the metal or alloy of the artifact and the receiving biological medium.

Attempts have been made to provide metallic artifacts with a biocompatibility as regards the tissues and the medium receiving them, by covering the artifacts with a glass or ceramic coating layer for example. The coating layers which have been developed have a relatively important thickness, of the order of a millimeter. In some cases, it has been possible to make thinner layers, the thickness of which may go down to the micron.

However, it appears that such coating layers having a thickness equal or in excess of a micron all correspond to a structure of a crystalline layer. So, when the practitioner shapes the artifact, or deforms the artifacts coated with such a layer when he places them in position, cracks may appear. The insulation expected from the deposition of the coating layer is therefore not ensured, nor is the biocompatibility with regards to the tissues receiving the artifact.

The aim of the invention is to remedy the disadvantages of said non deformable coating layers, and to provide metallic artifacts with a biocompatibility with regards to the tissues receiving them.

The object of the invention is a method for making artifacts usable in vivo, of the type in which a metallic armature is covered with a coating layer made of a biocompatible compound, wherein the compound forming the layer is insulating, refractory, amorphous and non porous, and wherein the thickness of said layer is between 100 A° and 0.5 micron.

According to the invention, the application of a thin layer is provided by a reactive or radio frequency cathodic sputtering operation for example.

Also according to the invention, the biocompatible insulating compound is chosen in the group comprising the ceramics, alumina, glasses, silica or quartz derivatives, apatites and their derivatives, oxides, aluminium nitrides and sulphides, and carbons.

A further object of the invention is also an artifact usable in vivo, of the type in which a metallic armature is covered with a coating layer made of a biocompatible compound, wherein said compound is insulating, refractory, amorphous and non porous, and wherein the thickness of the coating layer is between 100 A° and 0.5 micron, so that the coating layer is capable of supporting without cracks the deformations of the artifact during the clinical phase.

The invention applies particularly to the making of artifacts usable in osseous surgery and buccal surgery. As an example, a prefabricated dental implant is brought to shape by the practitioner at the moment where it is placed in position. During this shaping operation, deformations and mechanical constraints are applied to the implant. If such an implant has been previously insulated with a layer of ceramic for example, having a thickness superior to one micron, the shaping operation may deteriorate the ceramic, and the biocompatibility of the implant is no more ensured.

On the contrary, according to the invention, a coating layer of a thickness between 100 A° and 0.5 micron remains non deformable, without the appearance of cracks, and does not present such a risk of being deteriorated.

The result is that the artifact once put in place, made of a prefabricated metallic armature and a layer of a biocompatible coating, offers all the desired security and biocompatibility guarantees.

The thin coating layer has a thickness comprised between about 100 Angströms and about 0.5 micron. It is applied for example by a reactive cathodic sputtering operation (bombardment of a target by a reactive gas in the form of a plasma), or by a radio frequency cathodic sputtering operation.

During the application phase of the coating layer on the artifact, it is necessary to use a pronounced vacuum in order to avoid the deposition of impurities which would affect the insulating character of the coating layer. It is in fact absolutely necessary that said layer be insulating, non porous, and of an amorphous structure. Then, it is non biodegradable, and it plays perfectly its part.

The originality of the method according to the invention consists in using the properties and advantages attached to the metallic nature of the implants while ensuring, due to the thin coating layer, the biocompatibility of the made artifacts with regards to the tissues intended for receiving them.

With such a method, the risk of a deterioration of the coating layer during the shaping or placing in position of the implant can be avoided.

The mechanical and physical characteristics of the metallic implants of the proposed coatings have also the advantage of offering a security for the future of their mutual connection.

The invention has been described in relation with the embodiment of dental implants, but it also applies to artifacts used in osseous surgery, be they prosthesis elements or fixation accessories for example, particularly osteo synthesis threads and plates.

The method according to the invention allows the elaboration of custom-made metallic artifacts, in as much as they are easy to cast, since the protecting layer insulates them from the biological medium and prevents oxidation and corrosion phenomena of the metals or alloys forming the artifacts.

I claim:

1. A method for making artifacts usable in vivo, of the type in which a metallic armature is covered with a coating layer of a biocompatible compound, wherein the compound forming said layer is insulating, refractory, amorphous and non porous, and wherein the thickness of said layer is between 100 A° and 0.5 micron.

2. A method according to claim 1, wherein the biocompatible insulating compound is chosen in the group comprising the ceramics, alumina, glasses, silica or quartz derivatives, apatites and their derivatives, oxides, aluminium nitrides and sulphides and carbons.

3. A method according to claims 1 and 2 taken together, wherein the application of the coating layer is provided by a reactive or radio frequency cathodic sputtering operation.

4. An artifact usable in vivo, comprising a metallic armature covered with a coating layer of a biocompatible compound, said compound being insulating, refractory, amorphous and non porous, and the thickness of the coating layer is between 100 A° and 0.5 micron, whereby the coating layer is adapted for supporting without cracks deformations of the artifact during the clinical phase and the coated artifact can be shaped and deformed during implantation in a patient without deteriorating or cracking the coating layer.

5. A surgical implant comprising a metallic armature,
 a biocompatible layer coated on said armature, said layer comprising at least one biocompatible insulating compound selected from the group consisting of ceramics, alumina, glasses, silica derivatives, oxides, aluminum nitrides, aluminum sulphides, and carbons, said coating having a thickness of between about 100 Angstroms and 0.5 microns and being applied by sputtering, and
 the coated implant being shapeable and deformable during implantation in a patient without causing deterioration or cracking of the coating layer.

* * * * *